United States Patent
Iaquaniello et al.

(10) Patent No.: US 9,340,494 B2
(45) Date of Patent: May 17, 2016

(54) PROCESS FOR PRODUCING AMMONIA AND UREA

(71) Applicant: STAMICARBON B.V. ACTING UNDER THE NAME OF MT INNOVATION CENTER, Sittard (NL)

(72) Inventors: Gaetano Iaquaniello, Rome (IT); Barbara Cucchiella, Rome (IT); Elena Antonetti, Rome (IT)

(73) Assignee: STAMICARBON B.V. ACTING UNDER THE NAME OF MT INNOVATION CENTER, Sittard (NL)

( * ) Notice: Subject to any disclaimer, the term of this patent is extended or adjusted under 35 U.S.C. 154(b) by 0 days.

(21) Appl. No.: 14/366,950

(22) PCT Filed: Dec. 18, 2012

(86) PCT No.: PCT/NL2012/050901
§ 371 (c)(1),
(2) Date: Jun. 19, 2014

(87) PCT Pub. No.: WO2013/095130
PCT Pub. Date: Jun. 27, 2013

(65) Prior Publication Data
US 2014/0364647 A1    Dec. 11, 2014

(30) Foreign Application Priority Data

Dec. 19, 2011  (EP) .................................... 11194377

(51) Int. Cl.
*C01C 1/04* (2006.01)
*C01B 3/02* (2006.01)
(Continued)

(52) U.S. Cl.
CPC ............... *C07C 273/10* (2013.01); *C01B 3/025* (2013.01); *C01B 3/26* (2013.01); *C01B 3/382* (2013.01);
(Continued)

(58) Field of Classification Search
CPC ............ C01B 3/025; C01B 3/382; C01C 1/04
USPC ....................................... 564/63, 69
See application file for complete search history.

(56) References Cited

U.S. PATENT DOCUMENTS 6,448,441 B1    9/2002  Wing-Chiu et al.
2001/0006615 A1 *  7/2001  Badano et al. ............ C01B 3/48
(Continued)

FOREIGN PATENT DOCUMENTS

GB  WO 2006117499 A1 * 11/2006  .............. C01B 3/382
WO  WO -2006/117499     11/2006
WO  WO 2006/117499   * 11/2006

OTHER PUBLICATIONS

International Preliminary Report on Patentability and Written Opinion for PCT/NL2012/050901, dated Jun. 24, 2014, 11 pages.
(Continued)

*Primary Examiner* — Kamal Saeed
*Assistant Examiner* — Janet L Coppins
(74) *Attorney, Agent, or Firm* — Morrison & Foerster LLP

(57) ABSTRACT

Disclosed is a process for the production of ammonia comprising a step wherein synthesis gas is formed in two different ways, viz. by catalytic partial oxidation (31) and by steam reforming, and wherein the combined streams of synthesis gas are subjected to a water gas shift reaction (50). Also disclosed is a process of producing urea, wherein ammonia is formed (90) in a process involving said combined streams and wherein carbon dioxide (110) formed in the same process is reacted with said ammonia so as to form urea.

18 Claims, 3 Drawing Sheets

(51) Int. Cl.
*C01B 3/38* (2006.01)
*C07C 273/10* (2006.01)
*C01B 3/48* (2006.01)
*C01B 3/26* (2006.01)

(52) U.S. Cl.
CPC ............... *C01B 3/384* (2013.01); *C01B 3/386* (2013.01); *C01B 3/48* (2013.01); *C01C 1/04* (2013.01); *C01B 2203/0233* (2013.01); *C01B 2203/0244* (2013.01); *C01B 2203/0261* (2013.01); *C01B 2203/0283* (2013.01); *C01B 2203/04* (2013.01); *C01B 2203/043* (2013.01); *C01B 2203/0445* (2013.01); *C01B 2203/0475* (2013.01); *C01B 2203/068* (2013.01); *C01B 2203/1241* (2013.01); *C01B 2203/141* (2013.01); *C01B 2203/146* (2013.01)

(56) References Cited

U.S. PATENT DOCUMENTS

2009/0064582 A1* 12/2009 Malhotra et al. .......... C01B 3/38
2011/0085967 A1* 4/2011 Raybold et al. ........... C01B 3/38
2011/0297886 A1 12/2011 Panza

OTHER PUBLICATIONS

International Search Report for PCT/NL2012/050901, mailed May 14, 2013, 5 pages.

* cited by examiner

PROCESS FOR PRODUCING AMMONIA AND UREA

CROSS-REFERENCE TO RELATED APPLICATIONS

This application is the national phase of PCT application PCT/NL2012/050901 having an international filing date of 18 Dec. 2012, which claims benefit of European patent application No. 11194377.5 filed 19 Dec. 2011. The contents of the above patent applications are incorporated by reference herein in their entirety.

FIELD OF THE INVENTION

The invention pertains to a process for the production of ammonia, as well as to a process for producing ammonia and, subsequently, urea.

BACKGROUND OF THE INVENTION

Ammonia is generally produced by reacting hydrogen and nitrogen, according to the following reaction equation:

$$3H_2 + N_2 \rightarrow 2NH_3$$

The $H_2$ is generally obtained from synthesis gas (normally known as "syngas"), which in turn is obtained from a hydrocarbon feed material, which is subjected to steam reforming, often followed by autothermal reforming (ATR) so as to produce a mixture comprising carbon monoxide (CO), hydrogen ($H_2$), and carbon dioxide ($CO_2$), usually followed by a water gas shift reaction wherein carbon monoxide reacts with water so as to form carbon dioxide and hydrogen. After removal of $CO_2$ (or otherwise separating $H_2$ from the gas mixture), the hydrogen is available for reaction with nitrogen ($N_2$). The latter is either present in the original gas mixture (as it is inert with respect to all steps preceding the ammonia synthesis conditions), or added later if obtained from air, in a unit separating nitrogen from oxygen. The hydrogen and nitrogen are subjected to compression and conversion into ammonia in a synthesis reactor.

Ammonia is frequently used as a starting material in the synthesis of urea. Urea ($NH_2CONH_2$) can be produced from ammonia and carbon dioxide at an elevated temperature of, typically, between 150° C. and 250° C. and an elevated pressure of, typically, between 12 and 40 MPa, in the synthesis zone of a urea plant. In this synthesis, two consecutive reaction steps can be considered to take place. In the first step ammonium carbamate is formed, and in the next step, this ammonium carbamate is dehydrated so as to give urea:

$$2NH_3 + CO_2 \rightarrow H_2N-CO-ONH_4 \quad (i)$$

$$H_2N-CO-ONH_4 \leftrightarrow H_2N-CO-NH_2 + H_2O \quad (ii)$$

A reference process, shown in FIG. 1, for producing ammonia comprises a steam reforming process for producing hydrogen followed by reaction of said hydrogen with nitrogen produced in an air separation unit (ASU). A disadvantage of this process however is that significant energy is used to separate the air into nitrogen and oxygen but no use is made of the oxygen so produced.

Another reference process, such a shown in U.S. Pat. No. 6,448,441, which is incorporated herein by reference, involves the use of two parallel gasifiers, working at different operating conditions, in order to increase the $CO_2$ rate for urea production when a natural gas gasifier is used to produce syngas. By using two gasifiers, it is possible to obtain the correct stoichiometry in the reaction mixture for subsequent production of ammonia. In the process of U.S. Pat. No. 6,448,441, there is a need to produce additional $CO_2$ to obtain the correct stoichiometry for the reaction of ammonia and $CO_2$ to nitrogen. This requires the combustion of additional carbonaceous material, for example natural gas, which consumes more raw materials and energy.

In the production of ammonia, as well as in the production of urea, it is thus desired to be able to present the starting material in the desired stoichiometry, and it is desired to reduce energy and material costs as much as possible.

SUMMARY OF THE INVENTION

In order to better address one or more of the foregoing desires, the invention presents, in one aspect, a process for the production of ammonia, comprising the steps of
(a) providing a hydrocarbon material;
(b) subjecting the hydrocarbon material to catalytic partial oxidation (CPO) so as to produce a CPO gas stream comprising carbon monoxide, hydrogen and carbon dioxide;
(c) providing an SR gas stream obtained by the steam-reforming (SR) of a hydrocarbon feed material;
(d) subjecting the CPO gas stream and the SR gas stream to a water gas shift (WGS) reaction so as to react carbon monoxide with water under the formation of a WGS gas comprising hydrogen and carbon dioxide;
(e) subjecting separate gas streams to a mixing step, either before or after the WGS reaction, so as to provide a mixed WGS gas;
(f) subjecting the mixed WGS gas to a hydrogen enrichment step so as to obtain a hydrogen enriched stream;
(g) reacting the hydrogen enriched stream with nitrogen under ammonia forming conditions, so as to produce ammonia.

In another aspect, the invention concerns a process for the preparation of urea, comprising a process for the preparation of ammonia as defined above, wherein the separation step (d) comprises removing $CO_2$ from the reaction mixture, and reacting the ammonia with the removed $CO_2$ under urea-forming conditions.

DETAILED DESCRIPTION OF THE INVENTION

Figure 1:
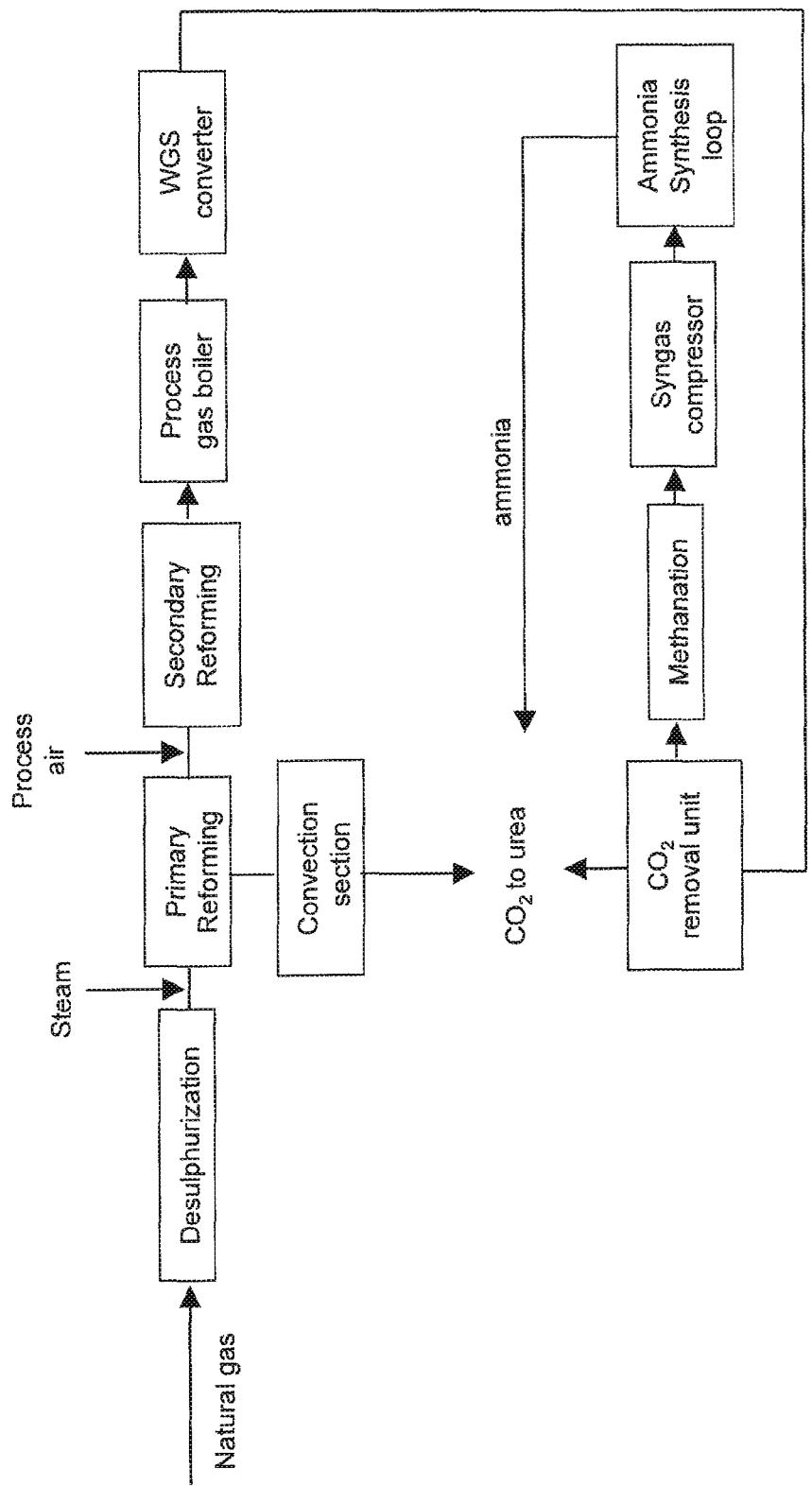
FIGS. 1 and 2 are schematic representations of embodiments known in the art

In a broad sense, the invention is based on the judicious insight that the use of catalytic partial oxidation (CPO) in the formation of synthesis gas, in combination with steam reforming, is able to bring about unexpected advantages in both the production of ammonia (leading to revamping ammonia production) and the production of urea, as a result of additional $CO_2$ production that can be used for increased urea production.

In order to increase the $CO_2$ rate for urea production, a portion of the conventional hydrocarbon feed to steam reforming is subjected to CPO, and is converted into a type of synthesis gas, in this description denoted "CPO gas" with a higher $CO/H_2$ ratio than would have been obtained in steam reforming. The resulting relatively higher amount of CO, is subsequently converted into $CO_2$ downstream in a water gas shift converter.

The production of ammonia requires the availability of nitrogen ($N_2$) as a reactant. Nitrogen is obtained from air, and in regular processes this results in oxygen ($O_2$) being lost. In the present invention, it is judiciously foreseen that oxygen yielded by providing nitrogen as a reactant, is used as the source of oxidation oxygen in the catalytic partial oxidation step and recovered to produce further urea.

Thus, the combination, according to the invention, of a catalytic partial oxidation step and a steam reforming step for the synthesis of ammonia, presents a highly economical advancement. This presents in fact a synergy, in the sense that the oxygen required for catalytic partial oxidation is available by virtue of the production of ammonia and, put otherwise, oxygen normally lost can now be used.

The CPO gas stream and the SR gas stream can be mixed prior to the WGS reaction. They can also be subjected to the WGS reaction separately, and then the resulting gas streams are mixed so as to provide a mixed WGS gas. Preferably, the process of the invention comprises the step of mixing the CPO gas and SR gas streams so as to provide a mixed gas, and subjecting the mixed gas to the WGS reaction. In a particularly preferred embodiment, the complete CPO gas and SR gas streams are subjected to WGS, and thus there is no stream by-passing the WGS reaction. The advantage of this embodiment is that the necessary stoichiometric ratio for the ammonia and, subsequently, urea production is already obtained from the two streams, which are completely subjected to WGS. Therefore, there is no need to bypass the WGS and use part of the CPO and SR gas streams for, e.g. hydrogen recovery, in order to adjust the composition before the ammonia synthesis reaction.

The production of urea requires the availability of carbon dioxide ($CO_2$) as a reactant. The problem of conventional urea production processes is that there is typically a deficit of $CO_2$ with respect to available ammonia. The present invention has an advantage that both ammonia and $CO_2$ are produced in the necessary amounts and are hence directly suitable for urea synthesis. Any $CO_2$ formed in the catalytic partial oxidation, and particularly from the subsequent step of a water gas shift reaction, is present in the stream of gases that is part of a production process, and is therewith directly available as a reactant for the production of urea.

The process of the invention, whether for producing ammonia or for producing urea, starts with the catalytic partial oxidation of a hydrocarbon material as well as steam reforming of a hydrocarbon material. The hydrocarbon material can be a single hydrocarbon, a mixture of hydrocarbons, or any other composition comprising at least one hydrocarbon. As conventional, in the event that natural gas is employed, this will generally be desulphurized before being subjected to the process of the invention.

The hydrocarbon material can be in a gaseous (e.g. methane or natural gas) and/or in a liquid state and also from biomass. The hydrocarbon material may be suitable for direct feed to the CPO or can be pre-treated for removal of any impurities, such as sulphur compounds, that might be present.

Preferably, the hydrocarbon material is selected from the group consisting of natural gas, Liquefied Petroleum Gas (LPG), refinery gas, naphtha, and mixtures thereof.

The SR part of the process according to the invention, is well-known to the skilled person. The CPO part will be elucidated in more detail hereinafter.

CPO reactors are known to the skilled person. A CPO reactor generally comprises a reaction zone, made up of a vertical cylindrically shaped steel pressure vessel lined with a refractory material. A CPO reactor typically is distinguished from an autothermal reformer reactor, as the latter comprises a burner, which a CPO generally does not.

A mixer, such as shown in WO2007045457 may be used to introduce feed streams into the reactor.

The CPO process results in synthesis gas, or syngas, comprising CO, $CO_2$ and $H_2$. This gas is also referred to as "CPO gas" in this description, With reference to methane as an exemplary hydrocarbon feed material, the reaction equation for the CPO process is:

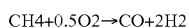

$$CH4+0.5O2 \rightarrow CO+2H2$$

The term CPO (also referred to as SCT-CPO) is known to the skilled person. SCT-CPO refers to Short Contact Time Catalytic Partial Oxidation. The CPO reaction takes place in a reactor under the influence of a catalyst at residence times between $10^{-2}$ to $10^{-4}$ and with typical catalyst surface contact times around $10^{-6}$ s$^{-1}$. These contact time correspond to typical space velocities of 100,000 to 250,000 hr$^{-1}$, preferably 100,000 to 200,000 hr$^{-1}$. Catalysts employed for SCT-CPO comprise Ni, Pd, Pt, Rh, or Ru. The reaction takes place at catalyst surface temperatures above 950° C., preferably above 1000° C. By employing said short contact times and high catalyst surface temperatures the formation of CO is highly favoured and the formation of carbon or CO2 is suppressed. This leads to a highly favourable synthesis gas composition, which in turn results in favourable stoichiometric conditions for both ammonia and urea production. The CPO reaction will generally be carried out in a catalytic partial oxidation reactor, comprising a suitable catalyst bed that serves to catalyze the partial oxidation of hydrocarbon into CO and $H_2$. It will be understood that some complete oxidation product (viz. $CO_2$) may also be formed. The term "CPO" is known to the skilled person, and catalysts achieving this are familiar. See for example L. Basini, Catalyst Today 117 (2006), 384-393 or L. Basini, K. Aasberg-Petersen, A. Guarinoni, M. Oestberg, Catalysis Today (2001) 64, 9-20 "Catalytic Partial Oxidation of Natural Gas at Elevated Pressure and Low Residence Time"; (c) H. Hickman, L. D. Schmidt, J. Catal. 138 (1992) 267; (d) D. Hichman, L. D. Schmidt Science, 259 (1993) 343; (e) L. Basini, G. Donati WO 9737929; (f) Sanfilippo, Domenico; Basini, Luca; Marchionna, Mario; EP-640559; (g) D. Schaddenhorst, R. J. Schoonebeek; WO 00/00426; (h) K. L. Hohn, L. D. Schmidt, S. Reyes, J. S. Freeley, WO 01/32556; (i) A. M. Gaffney, R. Songer, R. Ostwald, D. Corbin, WO 01/36323.

It will be understood, that in a CPO process, oxygen is to be provided in order to effect the oxidation. Whilst the oxygen can be in the form of air, a drawback thereof is that this means that a relatively large amount of nitrogen, which is inert until the ammonia-forming reaction, will have to be carried through the process. This requires a much larger equipment than would be strictly necessary for the reactions to be conducted, which is economically undesirable, and is associated with other drawbacks such as a need for building a facility occupying an unduly large ground surface area In this respect it is preferred that the catalytic partial oxidation is conducted under the influence of an oxygen-containing gas-stream comprising at least 40% oxygen, preferably at least 60% oxygen. More preferably, the oxygen-containing gas-stream is oxygen having a purity of from 90%-100%.

A further advantage of using catalytic partial oxidation, is that a synthesis gas can be produced having the proper $H_2/CO_2$ ratio to maximize the yield of ammonia and urea in relation to the feed composition. By properly setting the steam to carbon (SC) and oxygen to carbon ($O_2$/C) ratio and preheating temperatures of the streams to the CPO reactor, also in presence of a natural gas feed, the amount of $CO_2$ produced in the synthesis gas is sufficiently high to use all of the produced $NH_3$, without excess of $NH_3$. The skilled person is aware, without undue experimentation, how to calculate the proper amounts of reactants needed in the synthesis gas, and how to set the catalytic partial oxidation process so as to achieve this.

The CPO reactor preferably is operated with a steam to carbon ratio (SC) in the range of 0.3-1.0, more preferably in the range of 0.4 to 0.6. The oxygen to carbon ratio (O/C) preferably is in the range of 0.3-1.0, more preferably in the range of 0.5-0.7.

In a further preferred embodiment, the raw gas obtained from the catalytic partial oxidation has a temperature between about 900° C. and 1200° C., preferably between 950-1050° C., better around 1000° C.

For the purpose of enhancing hydrogen production, the CPO reaction mixture, i.e. the CPO gas, is subjected to a water gas shift reaction. To this end, the mixture is routed to a water gas shift (WGS), wherein the gas mixture comprising carbon monoxide and steam is converted to hydrogen and carbon dioxide. The synthesis gas is generally cooled down, either in a process gas boiler or in a direct quencher, before entering the WGS reactor, producing a shifted synthesis gas stream. In the above example, starting from $CH_4$, this subsequent step of converting CO into $CO_2$ by means of a WGS reactor is represented by the following reaction equation:

$$CO+2H_2+H_2O \rightarrow CO_2+3H_2$$

The WGS reaction is typically carried out using either a single stage or multi stage to attain the desired degree and rate of conversion. In a multi stage process, the high temperature stage (HTS) operates at 300-450° C. and typically in the presence of an iron-based catalyst such as Fe/Cr. In the HTS the largest amount of CO is converted, usually more than 90% such as between 96 and 98%. The following stage can be a high, medium or low temperature stage (HTS, MTS or LTS); using MTS or LTS, the operating temperature is about 180-280° C. and typically a copper/zinc catalyst supported on alumina (Cu/Zn/Al) catalyst is used. In these latter stages the residual CO concentration in the outlet stream is typically as low as 0.1-0.3%.

The gas stream resulting from the WGS reactor contains mainly hydrogen, nitrogen and carbon dioxide. This gas stream is subjected to a hydrogen enrichment step so as to obtain a hydrogen enriched stream. The hydrogen enrichment step comprises separating hydrogen from carbon dioxide, e.g. by removing the latter. Optionally, hydrogen is separated from the WGS gas stream by pressure swing absorption (PSA) to yield a pure hydrogen stream and a purge gas stream (which typically comprises $H_2$, $CH_4$, CO, and $CO_2$). The purge gas from PSA is recycled to the CPO reactor in order to have a 100% conversion of the feed.

In a first aspect, the process of the invention is used for the production of ammonia. Particularly, the process of the invention is used for the purpose of enhancing the $CO_2$ content in the production of ammonia followed by the production of urea.

Producing ammonia requires providing hydrogen as a reactant, in accordance with the aforementioned step (e), viz. separating hydrogen from the reaction mixture. Preferably, the separation of hydrogen from the reaction mixture resulting from the water gas shift reaction, is executed by removing $CO_2$ from the gas mixture comprising hydrogen and carbon dioxide, so as to obtain a gas mixture enriched in $H_2$. The latter is reacted with $N_2$ so as to form ammonia. This reaction is well-known, and the skilled person is familiar with production methods and plants to carry this out.

In the process of the invention it is preferred that the oxygen used in the catalytic partial oxidation and the nitrogen used in the ammonia-forming reaction are obtained from an air separation unit. This brings about the advantage that no nitrogen needs to be carried through in the process, and the components of the air separated both are used to the maximum extent possible, rather than venting oxygen (in the case of using nitrogen in the ammonia-forming reaction) or burdening the process with a large amount of inert nitrogen (in the case of using air in the catalytic partial oxidation).

In an air separation unit, nitrogen and oxygen are produced generally according to the following equation:

$$1.88N_2+0.5O_2 \text{ (air)} \rightarrow 1.88N_2+0.5O_2$$

Air separation units (commonly known as ASUs) are known to the skilled person. Air separation units employing cryogenic, adsorption air separation, vacuum swing adsorption or membrane air separation may be used. In a preferred embodiment a cryogenic air separation process is used as it can yield highly pure nitrogen and oxygen. In the process large volumes of air from the atmosphere are compressed, cooled and liquefied. After compression impurities are removed and the nitrogen and oxygen are separated by distillation. A comprehensive overview may be found in the Nexant PERP 08/09S1 (February 2010) report. It will be understood that the oxygen and the nitrogen can also be produced in different air separation units. Preferably, the nitrogen and the oxygen used in the process come from the same air separation unit.

In a second aspect, the process of the invention is used for the production of urea. Particularly, the process of the invention is used for enhancing the production of urea in an existing unit. More particularly the process of the invention may be used for enhancing the production of urea in an existing unit by eliminating any excess of $NH_3$ or any excess of $CO_2$. In accordance with the invention, the ammonia is reacted with the aforementioned removed $CO_2$ under urea-forming conditions. This reaction too is well-known, and production methods and plants are available to the skilled person.

In a further aspect, the invention provides a method for enhancing the production of urea in an existing urea production coupled to a syngas production system comprising a steam reformer, by adding a CPO reactor to the syngas production system in parallel to the steam reformer.

Urea production plants are usually coupled to a syngas/hydrogen production plant and an ammonia plant for the synthesis of the reagents for urea production. A problem of syngas/hydrogen production plants comprising steam reformers is that with time the capacity of the steam reformers decreases due to intensive exploitation at high temperatures. Steam reformers typically contain tubes filled with catalyst that are subjected to very high temperatures, e.g. above 1000° C. for an extended period of time. A typical lifetime of such tubes is 15-20 years, however in practice the decrease in capacity begins much earlier, such as already after 10 years. At the same time, the capacity of the WGS reactor downstream of the SR and the capacity of other facilities like ammonia synthesis and urea synthesis reactors does not change over time. In total, the capacity of the whole urea production decreases due to the capacity decrease in the syngas/hydrogen production facility.

The present invention provides a solution to this capacity decrease of a urea plant coupled to a hydrogen production facility comprising a steam reformer, which is caused by the aging of the steam reformer. In particular, the invention provides a method for enhancing the production of urea in an existing urea production coupled to a syngas production system comprising a steam reformer (SR), by adding a catalytic partial oxidation (CPO) reactor to the syngas production system in parallel to the steam reformer. The described revamping allows to increase, or restore the capacity of the urea plant back to the initial capacity, without any alteration needed for the WGS reactor or other sections. Moreover, the capacity of the urea plant can even be increased to values higher than the initial capacity, due to a better stoichiometric ratio of the feed supplied to the ammonia and urea synthesis sections. The CPO reactor is relatively compact, has a small footprint and low investment costs compared to a steam reformer. In a preferred embodiment, the invention relates to a method for enhancing the production of urea in an existing urea production coupled to a syngas production system comprising a steam reformer and an autothermal reactor (SR+ATR), by adding a CPO reactor to the syngas production system in parallel to the steam reformer and autothermal reactor.

The existing urea plant preferably comprises an ASU in order to produce and effectively use nitrogen en oxygen in the process of the invention, as described above. Other preferred embodiments and process parameters described in this description apply equally to the method for enhancing the production of urea according to the invention.

Urea ($NH_2CONH_2$) can be produced from ammonia and carbon dioxide at an elevated temperature (typically, between 150° C. and 250° C.) and elevated pressure (typically between 12 and 40 MPa) in the synthesis zone of a urea plant. In this synthesis, two consecutive reaction steps can be considered to take place. In the first step ammonium carbamate is formed, and in the next step, this ammonium carbamate is dehydrated so as to give urea, The first step (i) is exothermic, and the second step can be represented as an endothermic equilibrium reaction (ii):

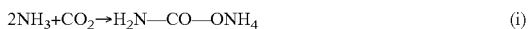
(i)

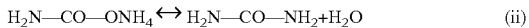
(ii)

In a typical urea production plant, the foregoing reactions are conducted in a urea synthesis section so as to result in an aqueous solution comprising urea. In one or more subsequent concentration sections, this solution is concentrated to eventually yield urea in a form of a melt rather than a solution. This melt is further subjected to one or more finishing steps, such as prilling, granulation, pelletizing or compacting.

By the judicious involvement of catalytic partial oxidation of part of the hydrocarbon feed, prior to a water gas shift reaction with another part of the hydrocarbon feed, and particularly in conjunction with the use of an air separation unit, the invention provides a very economical way of using the components of the gas mixture obtained, in enhancing the production of urea without recovering $CO_2$ from the flue gases resulting from Steam Reforming (SR). The excess of nitrogen from the air separation unit may be used within the production facilities or sold to other users.

In the invention, as described above, two processes for producing synthesis gas (CPO gas and SR gas) are used in combination. It is possible, to carry through this splitting in advance, by just providing two different streams of hydrocarbon feed. These may be just different hydrocarbon feeds, of different source and/or composition. These may also be two hydrocarbon feeds from the same source and composition. Preferably, a single hydrocarbon feed stream is provided, which is then split into one stream subjected to CPO and another stream subjected to SR.

The relative amounts of the two streams are generally in a ratio of CPO-stream, SR-stream ranging from 1.2 to 0.8, preferably from 1.1 to 0.9 and most preferably from 1.05 to 0.95 (vol %/vol %). These stream ratios allow to achieve a favorable stoichiometric ratio necessary for the ammonia synthesis reaction and further in the process, urea synthesis reaction. As mentioned above, one of the advantages of the present invention is that using two streams—a CPO-stream and a SR-stream, which are treated in a WGS reactor, wherein both streams are preferably completely subjected to the WGS reaction, it is possible to achieve the necessary ratio of reagents for ammonia and urea production.

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a" or "an", "the", this includes a plural of that noun unless something else is specifically stated. Unless otherwise indicated percentages are volume percent and ratios (for example Steam/Carbon or Oxygen/Carbon) are on a vol % vol % basis.

DETAILED DESCRIPTION OF THE DRAWINGS

In FIG. 1 a typical representation is given of an embodiment known in the art.

A feed gas stream enters a desulphurization unit. The resulting stream is mixed with steam and fed to the steam reforming reactor (SR).

The syngas (SR gas) at the outlet of SR is introduced into the secondary reforming together with the process air stream. The syngas mixture enters the HTS and LTS WGS reactor stages, where CO present in the syngas is almost totally converted into $CO_2$ and further $H_2$.

The resulting shifted gas is cooled down and introduced into the $CO_2$ removal unit and then into a methanation reactor where the residual $CO/CO_2$ is converted in $CH_4$. The resulting 112 enriched stream, together with $N_2$ present as an inert to the preceding steps (with the $H_2/N_2$ mixture adjusted to the proper ratio if needed) is cooled, compressed and introduced into a ammonia synthesis reactor. In order to have a better stoichiometric ratio between $NH_3$ and $CO_2$ for urea production, the $CO_2$ contained into the flue gas is recovered, compressed and routed to the urea production to enhance its production.

Figure 2:
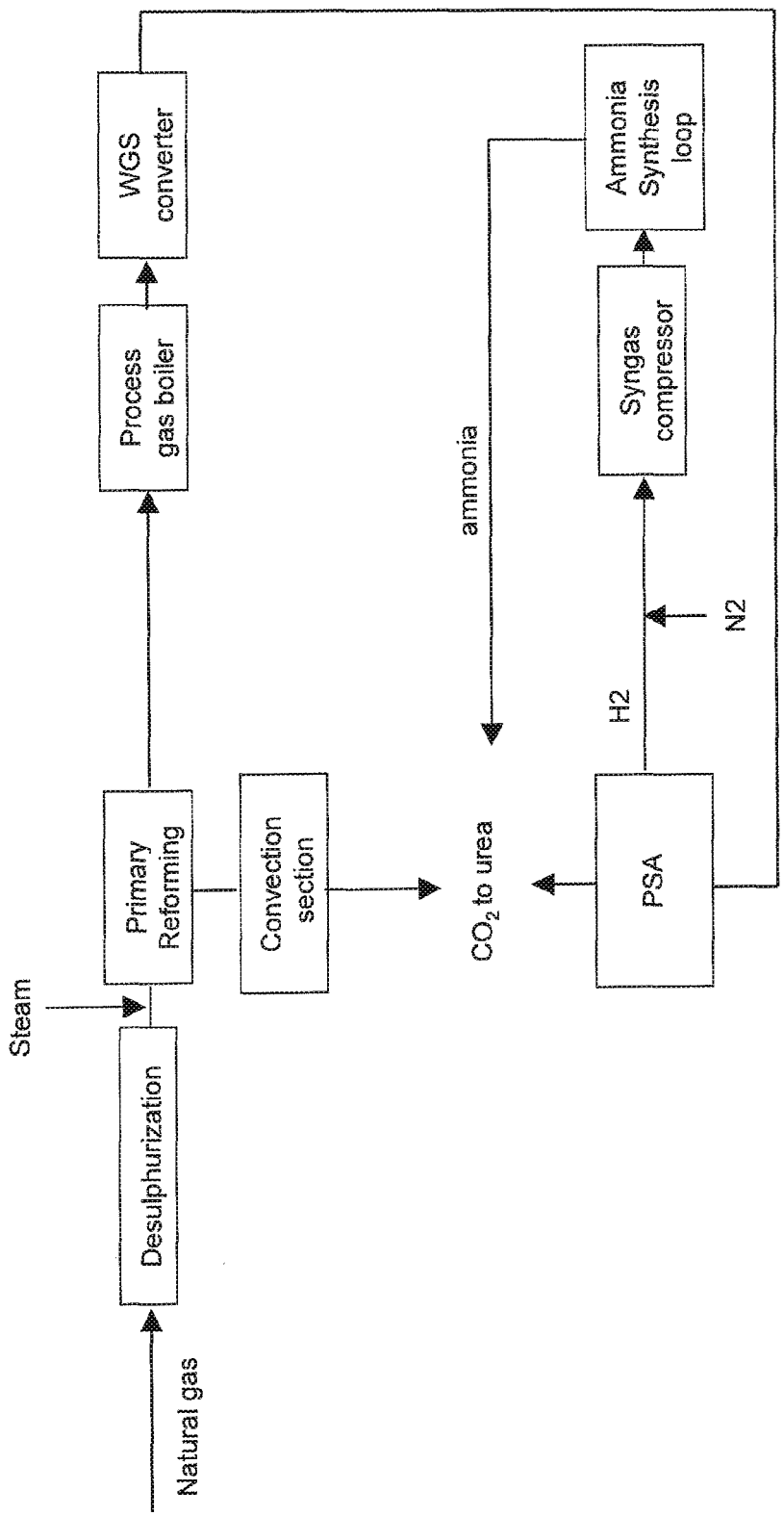

In FIG. 2 another embodiment of the prior art is given. As compared to FIG. 1, here a steam reformer alone produces $H_2$, and $N_2$ is added downstream.

Figure 3:
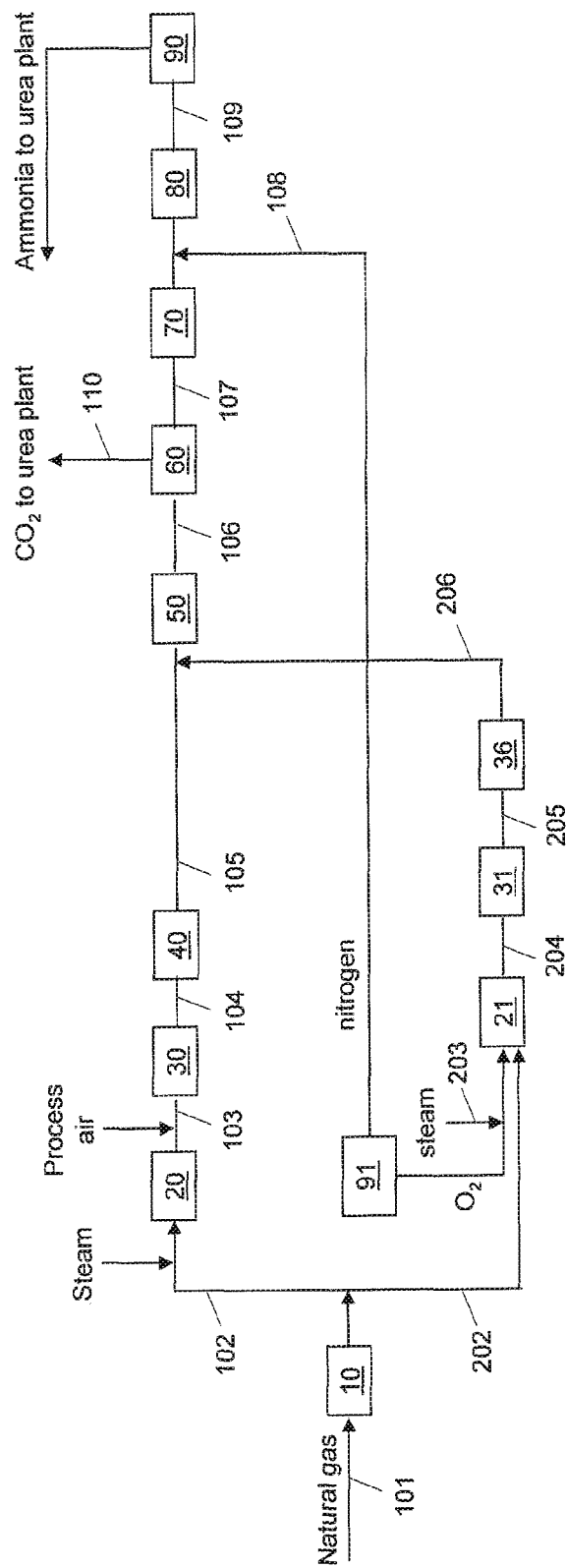
FIG. 3 is a schematic representation of an embodiment of the invention

In FIG. 3, one embodiment of the present invention is presented. A feed gas stream 101 enters a desulphurization unit 10 and then is split in two streams. A first stream 102 goes to a conventional plant based on steam reforming as described with reference to FIG. 1, Units 20, 30 and 40 correspond to a primary reformer, a secondary reformer and a process gas boiler respectively. A second stream with the remaining desulphurized feed goes to the CPO section, 202. The stream 202 is mixed in a suitable mixer, 21, with another stream containing oxygen and steam 203 before being fed to the CPO reactor 31. In one embodiment of the present invention, a pre-reformer (not shown) is upstream of CPO reactor 31.

The CPO reactor 31 may be a steel vessel internally lined for converting hydrocarbons, such as natural gas, LPG, refinery gas, naphtha and even heavier feed. The CPO reactor preferably operates with a steam to carbon ratio (SC) in the range of 0.3-1.0, preferably in the range of 0.4 to 0.6. The oxygen to carbon ratio ($O_2/C$) preferably is in the range of 0.4-1.0, more preferably in the range of 0.5-0.7.

The CPO gas at the outlet of the CPO reactor preferably is in the temperature range of 800° C.-1200° C., more preferably between 900° C. and 1050° C. The stream 205 is cooled by indirect heat exchange raising steam in a process gas boiler 36 (in an alternative embodiment it may be cooled by a direct water quenching). The cooled CPO gas 206 is then introduced into a common CO WGS reactor 50. The WGS reactor 50 may be in one stage or two stages with an intercooler (in an alternative embodiment it may be an isothermal shift convertor). WGS reactor 50 typically uses, e.g. an iron based catalyst and/or a copper based catalyst.

The resulting shifted gas 106 is cooled down and introduced into a $CO_2$ removal unit 60 where all of the $CO_2$ goes into a stream 110. The $CO_2$ removal unit 60 may be a solvent wash system, such as amine, selexol or other known solvents, or by other means known to the skilled person. The amount of $CO_2$ due to the addition of the CPO section, is maximized to enhance the urea production.

The stream resulting from the $CO_2$ removal, 107 is then purified into the methanation reactor 70, mixed with stream 108, compressed in unit 80 and routed to the ammonia synthesis reactor, 90.

The present invention enables to increase up to 10% the total carbon dioxide generation from high pressure process gas mixture produced by the process of the invention as opposed to the more conventional steam reforming (SR) technology. The carbon dioxide recovery from a high pressure process gas stream is much easier, without major severe corrosion issues and it is much less expensive. Utility and energy requirements are significantly lower compared to flue gas $CO_2$ recovery systems.

Nitrogen is obtained from the Air Separation Unit (ASU) 91 where also the oxygen stream 203 is produced. In another embodiment streams 108 and 203 are produced in different ASUs. As embodied herein, any process for ammonia synthesis may be used. The most common industrial process for ammonia synthesis involves forming a mixture of gaseous nitrogen and hydrogen in a 1 to 3 molar ratio, plus minor components as $CH_4$ and $CO_2$.

The present invention allows to enhance the urea production by at least 10%.

The produced ammonia is then combined with the $CO_2$ removed to form stream 106 and sent to a urea production unit. As embodied herein, any process for urea synthesis may be used.

The invention claimed is:

1. A process for the production of ammonia, comprising the steps of
   (a) providing a hydrocarbon material;
   (b) subjecting the hydrocarbon material to catalytic partial oxidation (CPO) so as to produce a CPO gas stream comprising carbon monoxide, hydrogen and carbon dioxide;
   (c) providing an SR gas stream obtained by the steam-reforming (SR) of a hydrocarbon feed material;
   (d) subjecting the CPO gas stream and the SR gas stream to a water gas shift (WGS) reaction so as to react carbon monoxide with water under the formation of a WGS gas comprising hydrogen and carbon dioxide;
   (e) subjecting separate gas streams to a mixing step, either before or after the WGS reaction, so as to provide a mixed WGS gas;
   (f) subjecting the mixed WGS gas to a hydrogen enrichment step so as to obtain a hydrogen enriched stream;
   (g) reacting the hydrogen enriched stream with nitrogen under ammonia forming conditions, so as to produce ammonia;

wherein the oxygen used in the catalytic partial oxidation and the nitrogen used in the ammonia-forming reaction are obtained from an air separation unit.

2. A process according to claim 1, comprising the step of mixing the CPO gas and SR gas streams so as to provide a mixed gas, and subjecting the mixed gas to the WGS reaction.

3. A process according to claim 1, wherein the mixed synthesis gas comprises synthesis gas from catalytic partial oxidation (CPO stream) and synthesis gas from steam reforming (SR stream) in a ratio CPO-stream:SR-stream ranging from 1.2 to 0.8 vol %/vol %.

4. A process according to claim 3, wherein the ratio CPO-stream:SR-stream is in a range of from 1.1 to 0.9 vol %/vol %.

5. A process according to claim 1, wherein the hydrocarbon material subjected to catalytic partial oxidation in step (b) and the hydrocarbon feed material in step (c) are split portions of the same hydrocarbon material provided in step (a).

6. A process according to claim 1, wherein the catalytic partial oxidation is conducted under the influence of an oxygen-containing gas-stream comprising at least 40% oxygen.

7. A process according to claim 6, wherein the oxygen-containing gas-stream is oxygen having a purity of from 90%-100%.

8. A process according to claim 1, wherein the hydrogen is separated from the reaction mixture by removing $CO_2$ from the CPO gas mixture, so as to obtain a gas mixture enriched in $H_2$.

9. A process according to claim 8, comprising a further purification of $H_2$ by methanation of CO and $CO_2$.

10. A process according to claim 8, wherein $H_2$ is purified using a Pressure Swing Absorber (PSA) after $CO_2$ removal, to yield a pure hydrogen stream and a purge gas stream 9, and wherein the purge gas from the PSA is recycled to the CPO reactor.

11. A process for the preparation of urea, comprising producing ammonia according to the process of claim 7, and reacting the ammonia with the removed $CO_2$, under urea-forming conditions.

12. A process according to claim 1, wherein the hydrocarbon material is selected from the group consisting of natural gas, Liquefied Petroleum Gas (LPG), refinery gas, naphtha, and mixtures thereof.

13. A process according to claim 1, wherein the oxygen to carbon ratio in the catalytic partial oxidation is between 0.3 and 0.7.

14. A process according to claim 1, wherein the raw gas obtained from the catalytic partial oxidation has a temperature between about 900° C. and 1200° C.

15. A process according to claim 1, wherein the CPO gas is first subjected to a steam generation heat exchanger and then to a WGS reaction, whereby the resulting stream is mixed with a WGS gas stream obtained from an existing SR unit.

16. A method for enhancing the production of urea in an existing urea production coupled to a syngas production system comprising a steam reformer (SR) and an autothermal reactor (ATR), by adding a catalytic partial oxidation (CPO) reactor to the syngas production system in parallel to the steam reformer and the ATR.

17. A process according to claim 4, wherein the ratio CPO-stream:SR-stream is in a range of from 1.05 to 0.95 vol %/vol %.

18. A process according to claim 6, wherein the catalytic partial oxidation is conducted under the influence of an oxygen-containing gas-stream comprising at least 60% oxygen.

* * * * *